United States Patent
Li et al.

(10) Patent No.: US 10,624,796 B2
(45) Date of Patent: Apr. 21, 2020

(54) BUILT-IN DETECTION DEVICE AND DETECTION METHOD THEREOF FOR DISPOSABLE DIAPERS

(71) Applicant: Chengdu Fanmi Technology Co., Ltd., Chengdu (CN)

(72) Inventors: Zhuodong Li, Chengdu (CN); Xiaobo Wang, Chengdu (CN); Zhongke Wang, Chengdu (CN); Bo Lai, Chengdu (CN); Hao Qu, Chengdu (CN); Shuai Wang, Chengdu (CN)

(73) Assignee: CHENGDU FANMI TECHNOLOGY CO., LTD., Chengdu (CN)

( * ) Notice: Subject to any disclaimer, the term of this patent is extended or adjusted under 35 U.S.C. 154(b) by 194 days.

(21) Appl. No.: 15/911,252

(22) Filed: Mar. 5, 2018

(65) Prior Publication Data
US 2019/0231608 A1   Aug. 1, 2019

(30) Foreign Application Priority Data

Jan. 31, 2018 (CN) .......................... 2018 1 0096636

(51) Int. Cl.
*A61F 13/42* (2006.01)
*G01N 27/04* (2006.01)
*H05K 1/18* (2006.01)

(52) U.S. Cl.
CPC ........... *A61F 13/42* (2013.01); *G01N 27/048* (2013.01); *A61F 2013/424* (2013.01);
(Continued)

(58) Field of Classification Search
CPC . A61F 13/42; A61F 2013/424; G01N 27/048; H05K 1/18; H05K 2201/10098;
(Continued)

(56) References Cited

U.S. PATENT DOCUMENTS 6,200,250 B1 * 3/2001 Janszen .................. A61F 13/42
493/334
10,299,723 B2 * 5/2019 Pepin .................. A61B 5/0002
(Continued)

FOREIGN PATENT DOCUMENTS

CN    106859857 A  *  6/2017
JP    2018068583 A  *  5/2018

*Primary Examiner* — Adnan Aziz
(74) *Attorney, Agent, or Firm* — Bayramoglu Law Offices LLC

(57) ABSTRACT

The present invention discloses a built-in detection device and a detection method thereof for disposable diapers which relates to the technical field of intelligent diapers and includes a circuit substrate attached inside the diaper and an alarm module placed outside the diaper, wherein the circuit substrate is provided with a core circuit region, a temperature sensor, a urine-wet sensor group and a bioelectrogenesis module. The core circuit region includes a power management module, a data acquisition module and a wireless transmitting module. The data acquisition module is electrically connected to the power management module, the urine-wet sensor group, the wireless transmitting module, and the temperature sensor, respectively. The power management module is electrically connected to the bioelectrogenesis module. The wireless transmitting module is connected to the alarm module in wireless transmission.

14 Claims, 5 Drawing Sheets

(52) U.S. Cl.
CPC ..... *H05K 1/18* (2013.01); *H05K 2201/10098* (2013.01); *H05K 2201/10151* (2013.01)

(58) Field of Classification Search
CPC .. H05K 2201/10151; H02J 7/32; G01D 21/02
See application file for complete search history.

(56) References Cited

U.S. PATENT DOCUMENTS

| | | | |
|---|---|---|---|
| 2004/0078219 A1* | 4/2004 | Kaylor | G06F 19/3418 705/2 |
| 2004/0220538 A1* | 11/2004 | Panopoulos | A61F 13/42 604/361 |
| 2008/0278337 A1* | 11/2008 | Huang | A61F 13/42 340/573.5 |
| 2011/0060299 A1* | 3/2011 | Wada | A61F 5/455 604/318 |
| 2011/0095884 A1* | 4/2011 | Xu | A61F 13/42 340/539.11 |
| 2013/0155631 A1* | 6/2013 | Yamauchi | H02N 2/181 361/748 |
| 2014/0200538 A1* | 7/2014 | Euliano | A61F 13/42 604/361 |
| 2015/0223706 A1* | 8/2015 | Raptis | A61B 5/0002 600/301 |

* cited by examiner

BUILT-IN DETECTION DEVICE AND DETECTION METHOD THEREOF FOR DISPOSABLE DIAPERS

CROSS REFERENCE TO RELATED APPLICATIONS

This application is based upon and claims priority to Chinese Patent Application 201810096636.9, field on Jan. 31, 2018, the entire content of which is incorporated herein by reference.

TECHNICAL FIELD

The present invention relates to the technical field of intelligent diapers, and particularly relates to a built-in detection device and a detection method thereof for disposable diapers.

BACKGROUND

With the continuous improvement in people's life quality, diapers become products which are thrown away after use and are mainly made of materials including non-woven fabrics, toilet paper, fluff pulp, super absorbent polymer, PE film, rubber band etc. Diapers are classified into two types i.e. special diapers for infants and special diapers for adults, which are mainly used to take care of infants, paralytics, patients with incontinence and old people with incontinence.

Diaper directly contacts user's skin, when in use. After the user urinates, the diaper absorbs a large amount of urine and becomes moist. At this time, the diaper requires changing by the nursing staff in time. Otherwise, the diaper may cause the skin area of user contacting with the diaper to become moist. The moist skin will become vulnerable and prone to suffer eczema. Moreover, wearing moist diaper for a long time can also cause discomfort to users. However, generally, the existing diapers do not have the real-time reminding function, so the nursing staff cannot be aware of the moist diapers in time, and thus would not change them in time, thereby resulting in poor wearing experience for people using the diapers.

In view of the foregoing defects, some diapers with reminding and alarming function are also available in the market. However, all available diapers can only sense the temperature, humidity and resistance inside the diaper through the built-in circuit to determine whether the user urinated or not, thereby causing inconvenience in practice. Moreover, the timely change of diapers cannot be guaranteed, and the installation process of the existing monitoring device built inside the diaper is more complex. Thus, the inconvenience in changing diapers is greatly increased, and the comfort of using diapers is affected.

Besides, the existing diapers can merely monitor whether the diapers are wet by the urine while the areas of the urine region of diaper cannot be determined. Therefore, the existing diapers are not humanized in practice, and are adverse to the large-scale promotion of the diapers with alarming and reminding function.

SUMMARY OF THE INVENTION

In order to solve the foregoing problems in the prior art, the objectives of the present invention are to provide a built-in detection device for disposable diapers and a detection method for the same to achieve the purpose that the diapers can determine the area of the urine-wet region and the volume of urine through the urine-wet sensing point by the self-power-generation of urine. By sensing the area of the urine-wetted region of the diaper, the use of diapers is more humanized, the change of diapers is convenient without affecting the comfortable degree of the diapers.

The technical solutions of the present invention are as follows. A built-in detection device for disposable diapers includes a circuit substrate attached inside the diaper and an alarm module disposed outside the diaper. The circuit substrate is provided with a core circuit region, a temperature sensor, a urine-wet sensor group and a bioelectrogenesis module. The core circuit region includes a power management module, a data acquisition module and a wireless transmitting module. The data acquisition module is electrically connected to the power management module, the urine-wet sensor group, the wireless transmitting module and the temperature sensor, respectively. The power management module is electrically connected to the bioelectrogenesis module. The wireless transmitting module is connected to the alarm module in wireless transmission.

Further, the bioelectrogenesis module includes a positive electric conduction sheet and a negative electric conduction sheet attached at a middle portion of the circuit substrate. The positive electric conduction sheet and the negative electric conduction sheet are made of different materials and are arranged with gap between them.

Further, the urine-wet sensor group includes a plurality of urine-wet sensing sheets uniformly distributed on a surface of the circuit substrate. The urine-wet sensing sheets and the positive electric conduction sheet are made of the same material, and each of the urine-wet sensing sheets is electrically connected to the data acquisition module.

Further, two opposite sides of the positive electric conduction sheet and the negative electric conduction sheet are both orthogonal-tooth-shaped, and the positive electric conduction sheet and the negative electric conduction sheet are engaged and matched with each other.

Further, the positive electric conduction sheet is made of a mixture of carbon and catalyst, and the negative electric conduction sheet is made of aluminum.

Further, the power management module includes a step-up circuit, a capacitor energy storing unit, a step-down circuit and an electricity quantity detecting unit. The bioelectrogenesis module is electrically connected to an input end of the step-up circuit, an output end of the step-up circuit is connected to the capacitor energy storing unit. The capacitor energy storing unit is electrically connected to an input end of the step-down circuit, and an output end of the step-down circuit is electrically connected to the data acquisition module. The capacitor energy storing unit is electrically connected to the electricity quantity detecting unit, and the electricity quantity detecting unit is connected to an enable end of the step-down circuit.

Further, a waterproof layer is coated above the core circuit region.

Further, the circuit substrate is provided with a plurality of urine-passing-holes.

Further, the alarm module includes a wireless receiving module, a main control chip and an alertor. The main control chip is electrically connected to the wireless receiving module and the alertor, respectively. The wireless receiving module is connected to the wireless transmitting module in wireless communication.

The present invention further provides a detection method of a built-in detection device for disposable diapers, which is implemented by the following steps:

(1) receiving original data from the wireless transmitting module by the alarm module and go to step (2);

(2) judging whether the original data is complete or not, if the original data is not complete, go back to step (1), if the original data is complete, go to step (3);

(3) converting the original data, obtaining a current temperature value, a current area value of the urine-wetted region and a current ID value stored in the data acquisition module of the diaper after the conversion, and go to step (4);

(4) judging whether the diaper is currently worn on a human body according to the temperature value in step (3); if a judgment result is "yes", the diaper is worn on the human body, then go to step (5); if the judgment result is "no", the diaper is not worn on a human body, then exit the judgment and go back to step (1), a state of the diaper remains unchanged;

(5) judging whether the diaper corresponding to the ID value has alarmed according to a parameter of the ID value in the step (3); if the judgment result is "yes", the diaper has alarmed, then go back to the step (1); if the judgment result is "no", the diaper has not alarmed, then go to step (6);

(6) judging whether a current urine-wetted degree of the diaper reaches a preset alarm threshold according to the area value of the urine-wetted region in step (3), if the judgment result is "yes", then go to step (7), if the judgment result is "no", then go back to step (1);

(7) alarming and prompting through the alarm module, and counting the ID value into an alarmed queue.

The advantages of the present invention are as follows.

1. In the present invention, the circuit substrate is attached inside the diaper so as to form a disposable structure, thus the change of diaper is convenient and quick and prevents any foreign matter sensation. After the diaper is wetted by urine, the bioelectrogenesis module carries out biological power generation under the action of the urine and supplies power to the overall circuit through the power management module without requiring the external battery to supply power, thereby preventing the waste battery from polluting the environment. Compared with the prior art, the present invention has the advantages of no radiation and reducing environmental pollution. Moreover, the detected data information is sent to the to the remote alarm module by the wireless transmitting module, which enables the nursing staff to monitor remotely.

2. A plurality of urine-wet sensing sheets are uniformly distributed on the circuit substrate for sensing the area of the urine-wetted region of the diaper. The urine-wet sensing sheet and the positive electric conduction sheet are made of the same material. When a region is wetted by urine, the voltage of the urine-wet sensing sheet at this region would increase. Whether this region is urine-wetted or not is determined by detecting the voltage and the area of the urine-wetted region of the diaper is calculated, to determine whether the alarm threshold is reached or not. By doing so, the use of the diapers becomes more humanized, and the situation where the diaper is blindly changed can be avoided.

3. Catalyst material is mixed inside the positive electric conduction sheet to achieve a better power-generating effect of the positive electric conduction sheet and the negative electric conduction sheet under the action of urine. Moreover, the two opposite sides of the positive electric conduction sheet and the negative electric conduction sheet are orthogonal-tooth-shaped, so as to increase the contact area between the positive electric conduction sheet and urine and the contact area between the negative electric conduction sheet and urine and improve the overall performance of bioelectrogenesis.

4. The power management module is provided with a step-up circuit and a step-down circuit, wherein the step-up circuit increases the voltage generated by the bioelectrogenesis, and the electrical energy is stored by the capacitor energy storing unit to reduce the requirement of the capacitance value of the capacitor energy storing unit, so as to reduce the size of the overall circuit. Therefore, the circuit can be packaged inside the diaper without causing foreign matter sensation. Meanwhile, the utilization rate of the electrical energy generated by the bioelectrogenesis can be improved through the step-up circuit. When the volume of urine is small and the voltage of the power-generation is low, the energy storage can also be realized by boosting the voltage, so as to ensure the normal operation of the entire circuit.

5. A large amount of urine-passing-holes are distributed on the circuit substrate to ensure that the water-absorbent properties of diapers are not be affected. Moreover, a waterproof layer is coated above the core circuit region to ensure that the internal circuit can work normally in a humid environment or in the urine.

DETAILED DESCRIPTION OF THE INVENTION

The present invention will be described in detail with reference to the drawings and specific embodiments hereinafter.

Figure 1:
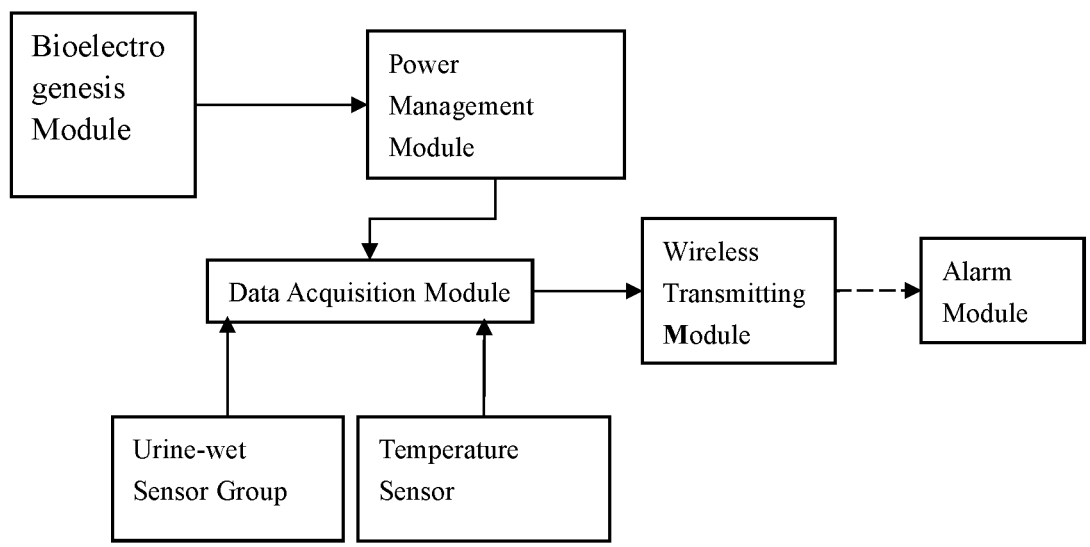
FIG. 1 is an overall system block diagram of a built-in detection device for disposable diapers provided by the present invention.
Figure 2:
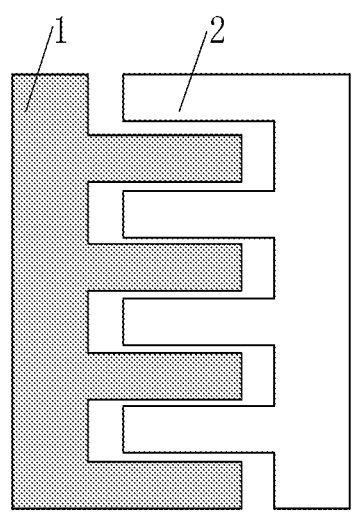
FIG. 2 is a structural schematic diagram of a bioelectrogenesis module in a built-in detection device for disposable diapers provided by the present invention.
Figure 3:
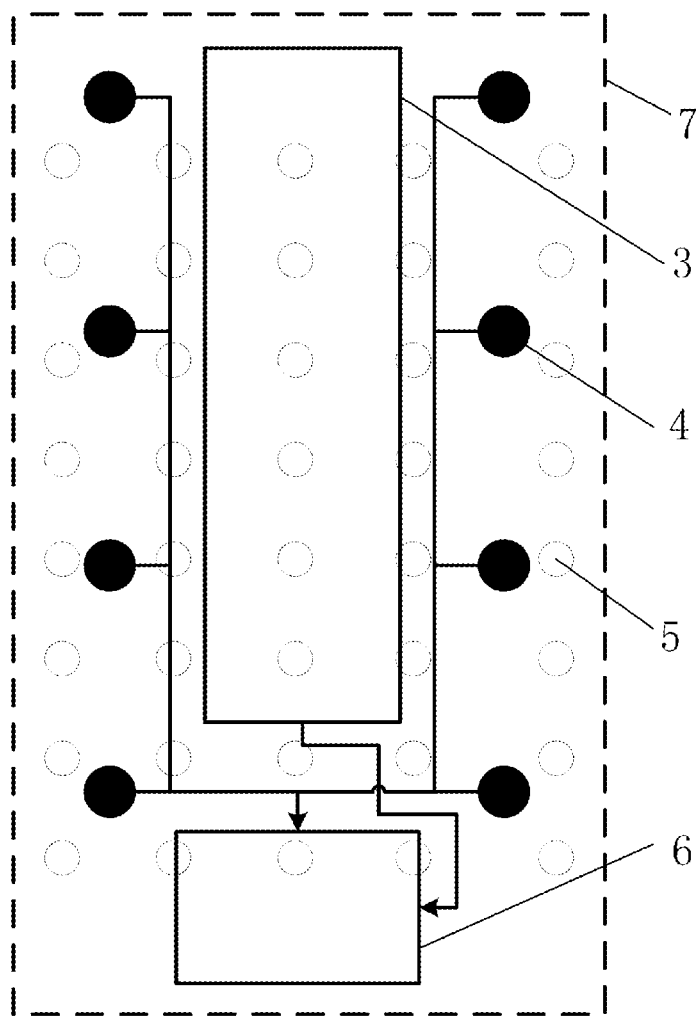
FIG. 3 is a schematic diagram of an overall structure layout of the built-in detection device for disposable diapers provided by the present invention.
Figure 4:
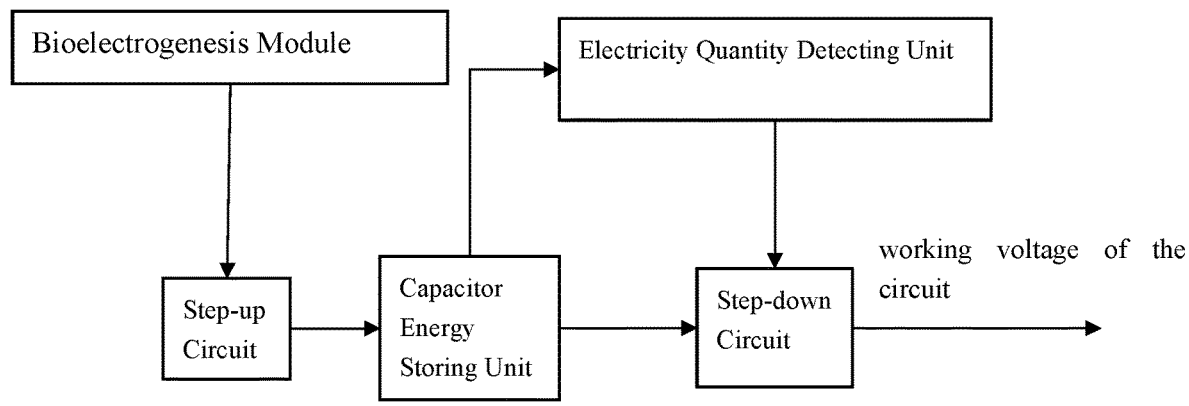
FIG. 4 is a system block diagram of a power management module in a built-in detection device for disposable diapers provided by the present invention.
Figure 5:
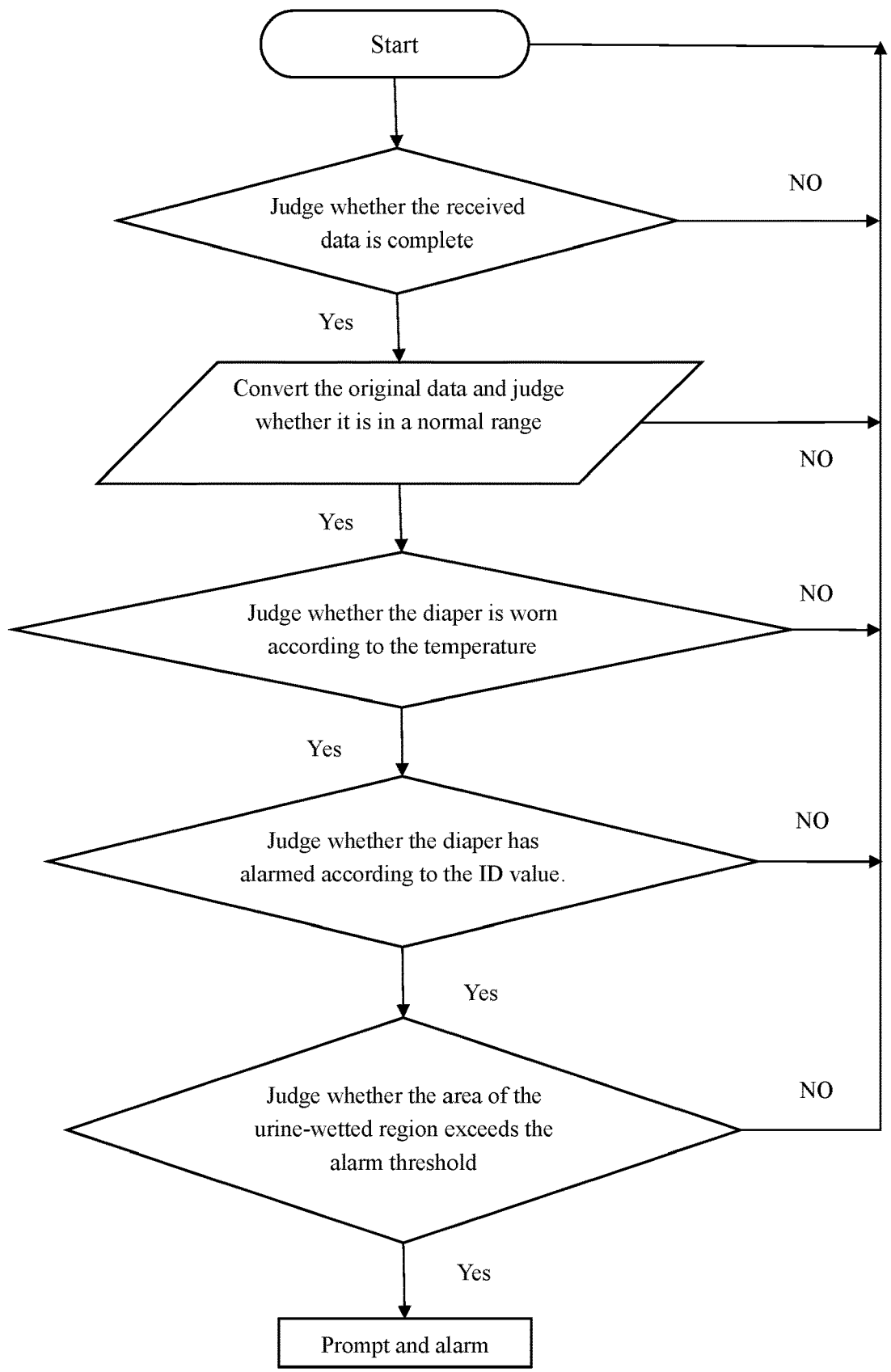
FIG. 5 is a step flowchart of a detection method of a built-in detection device for disposable diapers provided by the present invention.

As shown in FIG. 1 to FIG. 5, the present invention provides a built-in detection device for disposable diapers including circuit substrate 7 attached inside the diaper and an alarm module placed outside the diaper. The circuit substrate 7 is provided with core circuit region 6, temperature sensor, urine-wet sensor group and bioelectrogenesis module 3. The core circuit region 6 includes a power management module, a data acquisition module and a wireless transmitting module. The data acquisition module is electrically connected to the power management module, the urine-wet sensor group, the wireless transmitting module and the temperature sensor, respectively. The temperature sensor is used to detect the temperature at the position attached to the skin. The temperature of the diaper is usually between 30 and 37 degrees when worn on a body, so that whether the diaper is normally worn or not can be determined. The power management module is electrically connected to the bioelectrogenesis module 3. The wireless transmitting module is connected to the alarm module in wireless communication. The wireless transmitting module transmits the detected temperature value data, area data of the urine-wetted region and ID values to the alarm module, and the wireless communication between the wireless transmitting module and the alarm module can be established through transmission methods such as Bluetooth/wifi/sub 1G etc. The ID values are stored in the data acquisition module. In detail, the ID values are stored in the control unit (MCU) of the data acquisition module. Each ID value is unique, so as to distinguish different diapers. Preferably, the material of the circuit substrate 7 can be PVC, PET, PI and FPC, so as to ensure the overall softness without affecting the experience of using the diaper. The bioelectrogenesis module 3 is located at the middle position of circuit substrate 7, and has a relatively larger area to ensure a stable power supply of bioelectrogenesis module 3. Preferably, the built-in detection device disclosed in this application is not limited to be used in diapers, it can also be used in sanitary napkins or sanitary cottons.

The bioelectrogenesis module 3 includes a positive electric conduction sheet 1 and a negative electric conduction sheet 2, which are attached to the middle portion of circuit substrate 7. The positive electric conduction sheet 1 and the negative electric conduction sheet 2 are made of different materials, and are arranged with gap between them. That is to say, the bioelectrogenesis module is formed by two unconnected electric conduction sheets which are made of different materials. Since the materials of the two electric conduction sheets are different, and the bioelectricity will be generated under the action of urine. Preferably, the range of the minimum distance between the positive electric conduction sheet 1 and the negative electric conduction sheet 2 is 0.1 mm to 15 mm, the thickness of the positive electric conduction sheet 1 and the thickness of the negative electric conduction sheet 2 are both less than 2 mm, so as to ensure the softness and comfort of the diaper.

The urine-wet sensor group includes a plurality of urine-wet sensing sheets 4 evenly distributed on a surface of the circuit substrate 7. The urine-wet sensing sheets 4 and the positive electric conduction sheet 1 are made of the same material, and each of the urine-wet sensing sheets 4 is electrically connected to the data acquisition module. Preferably, generally, four or eight urine-wet sensing sheets 4 are used. The more pieces the urine-wet sensing sheets 4 are triggered by the urine, the larger area of the diaper is wetted. Here, the principle of the urine-wet sensing sheet is the principle of power generation. The material of the urine-wet sensing sheet 4 is the material of the positive electric conduction sheet 1 in the bioelectrogenesis module 3. When a region is wetted by urine, the voltage of the urine-wet sensing sheet 4 at this region would increase. The data acquisition module determines whether the diaper is wetted by urine or not by detecting the voltage.

The two opposite sides of the positive electric conduction sheet 1 and the negative electric conduction sheet 2 are both orthogonal-tooth-shaped, and the positive electric conduction sheet 1 and the negative electric conduction sheet 2 are engaged and matched with each other. By using the shape of orthogonal tooth, the contact area between the positive electric conduction sheet 1 and the urine and the contact area between the negative electric conduction sheet 2 and the urine can be increased, so as to increase the electrical energy generated by the bioelectrogenesis, and ensure that the capacitor power storing unit in the power management module gets charged normally. Apparently, the two opposite sides of the positive electric conduction sheet 1 and the negative electric conduction sheet 2 being orthogonal-tooth-shaped is merely the preferred technical solution of the present embodiment, the positive electric conduction sheet 1 and the negative electric conduction sheet 2 can also be configured with other shapes.

The positive electric conduction sheet 1 is made of a mixture of carbon and a catalyst, and the negative electric conduction sheet 2 is made of aluminum. Preferably, manganese dioxide is used as the catalyst to accelerate the bioelectrogenesis reaction. By doing so, the power supply capability of the bioelectricity becomes stronger (since the internal resistance is reduced, the supplied current is increased). During processing, the manganese dioxide and the electrical-conducting carbon slurry are uniformly mixed, and the mixed electrical-conducting carbon slurry is printed on the circuit substrate 7 by the method of printing. After that, a low temperature drying is used to make the mixed electrical-conducting carbon slurry to be fixed and shaped to form the positive electric conduction sheet 1. While aluminum is etched into a desired shape to be attached on the circuit substrate 7 to form the negative electric conduction sheet 2 by the method of etching. However, the catalyst is not limited to manganese dioxide, other catalytic materials are also acceptable. Certainly, the positive electric conduction sheet 1 made of carbon and the negative electric conduction sheet 2 made of aluminum are merely the preferred technical solution of the present embodiment. The positive electric conduction sheet 1 and the negative electric conduction sheet 2 can also be made of other materials.

The power management module includes a step-up circuit, a capacitor energy storing unit, a step-down circuit and an electricity quantity detecting unit. The bioelectrogenesis module 3 is electrically connected to the input end of the step-up circuit. The output end of the step-up circuit is connected to the capacitor energy storing unit. The capacitor energy storing unit is electrically connected to the input end of the step-down circuit. The output end of the step-down circuit is electrically connected to the data acquisition module. The step-down circuit reduces the voltage to the working voltage of the circuit. The capacitor energy storing unit is electrically connected to the electricity quantity detecting unit. The electricity quantity detecting unit is connected to the enable end of the step-down circuit. Preferably, the capacitor energy storing unit is a super capacitor energy storing device. Preferably, the overall circuit is designed as a chip to reduce the production costs in mass production and size of the circuit.

The working principle of the power management module is as follows. The step-up circuit converts the electrical energy generated by the bioelectrogenesis module 3 into a higher voltage and the electrical energy is stored through the capacitor energy storing unit. The electricity quantity detecting unit is used to detect the current electrical energy stored in the capacitor energy storing unit. When the stored electrical energy reaches the threshold, the electricity quantity detecting unit controls the enable end of the step-down circuit to start the step-down circuit. The enable end is an input pin of the step-down circuit. Only when the input pin is activated, the step-down circuit can start to work to supply power to the data acquisition module and the wireless transmitting module. After a data acquisition and transmission is completed, the electrical energy stored in the capacitor energy storing unit drops, and the electricity quantity detecting unit controls the enable end of the step-down circuit to stop the step-down circuit and cut off the power supply to the data acquisition module. The step-down circuit is subsequently started until the stored electrical energy reaches the threshold.

The functions of the above-mentioned circuit are as follows. On one hand, the use of the step-up circuit make the voltage generated by the bioelectrogenesis module 3 increased, and the electrical energy is stored by the capacitor energy storing unit to reduce the requirement for the capacitance value of the capacitor energy storing unit (According to the capacitance equation C=Q/U, it can be known that under the action of the same amount of the electricity, the higher the voltage, the smaller the required value of capacitance), so as to reduce the size of the overall circuit and make it can be packaged inside the diaper. On the other hand, the utilization rate of electrical energy generated by the bioelectrogenesis is improved through the step-up circuit. When the volume of urine is small and the voltage of the generated electricity is low, the energy can be stored by boosting the voltage to ensure the normal power supply of the overall circuit.

A waterproof layer is coated above the core circuit region 6 to ensure that the circuit can work normally in the humid environment or urine.

The circuit substrate 7 is provided with a plurality of urine-passing-holes 5, and a large amount of urine-passing-holes 5 are distributed on the circuit substrate 7 to ensure that the water-absorption property of the diaper is not affected, and the urine can permeate through the urine-passing-holes 5 to the interior of the diaper.

The alarm module includes a wireless receiving module, a main control chip and an alertor. The main control chip is electrically connected to the wireless receiving module and the alertor, respectively and the wireless receiving module is connected to the wireless transmitting module in wireless communication. Preferably, the alertor is configured as an audio and visual alertor or a buzzer alarm. Alternatively, the alarm module can also be substituted by a mobile terminal, and the mobile terminal can inform whether the diaper needs to be changed or not through the interactive interface.

The present invention also provides a detection method of a built-in detection device for disposable diapers, which is implemented by the steps below.

(1) The alarm module receives the original data from the wireless transmitting module and go to the step (2);

(2) Whether the original data is complete is judged by the main control chip in the alarm module, if the original data is incomplete, the operation is finished, then continue to wait for the data, when new data is imported, the judgement is continued; if the original data is complete, go to step (3) directly;

(3) The original data is converted, and the current temperature value, the current area value of urine-wetted region and the ID values stored in the data acquisition module of the diaper are acquired after the conversion, then whether the temperature value, the area value of urine-wetted region and the ID values are within a normal range is determined; if the judgment result is "yes", go to step (4); if the judgment result is "no", return to step (1);

(4) Whether the diaper is currently worn on a human body is judged according to the temperature value obtained in step (3); if the judgment result is "yes", the diaper is worn on a human body, and go to step (5); if the judgment result is "no", the diaper is not worn on a human body, then exit the judgment and return to step (1), the state of diaper remains unchanged;

(5) Whether the diaper corresponding to the ID value has alarmed is judged according to the parameter of the ID value obtained in the step (3); if the judgment result is "yes", the diaper has alarmed and return to the step (1); if the judgment result is "no", the diaper has not been alarmed and go to step (6);

(6) Whether the current urine-wetted degree of the diaper reaches a preset alarm threshold according to the area value of the urine-wetted region of the diaper; if the judgment result is "yes", go to step (7); if the judgment result is "no", return to step (1);

(7) Alarming and prompting are performed through the alarm module, the operation of the alertor is controlled through the main control chip to realize the function of alarming and prompting, and the ID values are counted into the alarmed queue, so that and the ID value will no longer be alarmed in next time, and then return to step (1).

The modules or sub-modules in the embodiment of the present invention may be a general integrated circuit such as a CPU (Central Processing Unit) or an ASIC (Application Specific Integrated Circuit).

The present invention is not limited to the foregoing alternative embodiments. Products in other forms can be derived by anyone with the teachings of the present invention. However, no matter what changes in shapes or structures are made, any technical solution falls into the scope defined by the appended claims of the present invention would fall within the protection scope of the present invention.

The invention claimed is:

1. A built-in detection device for disposable diapers, comprising:
   a circuit substrate attached inside a diaper; and
   an alarm module placed outside the diaper; wherein
   the circuit substrate is provided with a core circuit region, a temperature sensor, a urine-wet sensor group and a bioelectrogenesis module;
   the core circuit region comprises a power management module, a data acquisition module and a wireless transmitting module;
   the data acquisition module is electrically connected to the power management module, the urine-wet sensor group, the wireless transmitting module and the temperature sensor, respectively;
   the power management module is electrically connected to the bioelectrogenesis module; and
   the wireless transmitting module is connected to the alarm module in wireless transmission;
   wherein,
   the bioelectrogenesis module comprises a positive electric conduction sheet and a negative electric conduction sheet attached to a middle portion of the circuit substrate;
   the positive electric conduction sheet and the negative electric conduction sheet are made of different materials; and
   the positive electric conduction sheet and the negative electric conduction sheet are arranged with a gap between the positive electric conduction sheet and the negative electric conduction sheet;
   wherein,
   the urine-wet sensor group further comprises a plurality of urine-wet sensing sheets uniformly distributed on a surface of the circuit substrate;
   the plurality of urine-wet sensing sheets and the positive electric conduction sheet of the bioelectrogenesis module are made of a same material; and
   each of the plurality of urine-wet sensing sheets is electrically connected to the data acquisition module.

2. The built-in detection device for disposable diapers according to claim 1, wherein two opposite sides of the positive electric conduction sheet and the negative electric conduction sheet are both orthogonal-tooth-shaped; and the positive electric conduction sheet and the negative electric conduction sheet are engaged and matched with each other.

3. The built-in detection device for disposable diapers according to claim 1, wherein the positive electric conduction sheet is made of a mixture of carbon and a catalyst, and the negative electric conduction sheet is made of aluminum.

4. The built-in detection device for disposable diapers according to claim 1, wherein the power management module further comprises a step-up circuit, a capacitor energy storing unit, a step-down circuit and a electricity quantity detecting unit;

the bioelectrogenesis module is electrically connected to an input end of the step-up circuit;

an output end of the step-up circuit is connected to the capacitor energy storing unit;

the capacitor energy storing unit is electrically connected to an input end of the step-down circuit;

an output end of the step-down circuit is electrically connected to the data acquisition module;

the capacitor energy storing unit is electrically connected to the electricity quantity detecting unit; and the electricity quantity detecting unit is electrically connected to an enable end of the step-down circuit.

5. The built-in detection device for disposable diapers according to claim 1, wherein a waterproof layer is coated above the core circuit region.

6. The built-in detection device for disposable diapers according to claim 1, wherein the circuit substrate is provided with a plurality of urine-passing-holes.

7. The built-in detection device for disposable diapers according to claim 1, wherein the alarm module further comprises a wireless receiving module, a main control chip and an alertor;

the main control chip is electrically connected to the wireless receiving module and the alertor, respectively; and the wireless receiving module is connected to the wireless transmitting module in wireless communication.

8. A detection method of a built-in detection device for disposable diapers used in the built-in detection device for disposable diapers according to claim 1, comprising:

(1) receiving original data from the wireless transmitting module by the alarm module and go to step (2);

(2) judging whether the original data is complete or not, if the original data is not complete, go back to step (1), if the original data is complete, go to step (3);

(3) converting the original data, obtaining a current temperature value, an area value of the urine-wetted region and a ID value stored in the data acquisition module of the diaper after the conversion, and go to step (4);

(4) judging whether the diaper is currently worn on a human body according to the temperature value in step (3); if a judgment result is "yes", the diaper is worn on the human body, then go to step (5); if the judgment result is "no", the diaper is not worn on a human body, then exit the judgment and go back to step (1), a state of the diaper remains unchanged;

(5) judging whether the diaper corresponding to the ID value has alarmed according to a parameter of the ID value in the step (3); if the judgment result is "yes", the diaper has alarmed, then return to the step (1); if the judgment result is "no", the diaper has not alarmed, then go to step (6);

(6) judging whether a current urine-wetted degree of the diaper reaches a preset alarm threshold according to the area value of the urine-wetted region in step (3), if the judgment result is "yes", then go to step (7), if the judgment result is "no", then return to step (1);

(7) alarming and prompting through the alarm module, and adding the ID value into an alarmed queue.

9. The detection method of a built-in detection device for disposable diapers according to claim 8 wherein, two opposite sides of the positive electric conduction sheet and the negative electric conduction sheet are both orthogonal-tooth-shaped; and the positive electric conduction sheet and the negative electric conduction sheet are engaged and matched with each other.

10. The detection method of a built-in detection device for disposable diapers according to claim 8, wherein, the positive electric conduction sheet is made of a mixture of carbon and a catalyst, and the negative electric conduction sheet is made of aluminum.

11. The detection method of a built-in detection device for disposable diapers according to claim 8, wherein, the power management module further comprises a step-up circuit, a capacitor energy storing unit, a step-down circuit and a electricity quantity detecting unit;

the bioelectrogenesis module is electrically connected to an input end of the step-up circuit;

an output end of the step-up circuit is connected to the capacitor energy storing unit;

the capacitor energy storing unit is electrically connected to an input end of the step-down circuit;

an output end of the step-down circuit is electrically connected to the data acquisition module;

the capacitor energy storing unit is electrically connected to the electricity quantity detecting unit; and the electricity quantity detecting unit is electrically connected to an enable end of the step-down circuit.

12. The detection method of a built-in detection device for disposable diapers according to claim 8, wherein, a waterproof layer is coated above the core circuit region.

13. The detection method of a built-in detection device for disposable diapers according to claim 8, wherein, the circuit substrate is provided with a plurality of urine-passing-holes.

14. The detection method of a built-in detection device for disposable diapers according to claim 8, wherein, the alarm module further comprises a wireless receiving module, a main control chip and an alertor;

the main control chip is electrically connected to the wireless receiving module and the alertor, respectively; and the wireless receiving module is connected to the wireless transmitting module in wireless communication.

* * * * *